United States Patent
Yow et al.

(10) Patent No.: US 9,814,652 B2
(45) Date of Patent: Nov. 14, 2017

(54) UNIVERSAL NEEDLEFREE BAG ACCESS DEVICE

(71) Applicant: CAREFUSION 303, INC., San Diego, CA (US)

(72) Inventors: D. Gregory Yow, Wake Forest, NC (US); John C. Phillips, New Hill, NC (US)

(73) Assignee: CAREFUSION 303, INC., San Diego, CA (US)

( * ) Notice: Subject to any disclaimer, the term of this patent is extended or adjusted under 35 U.S.C. 154(b) by 81 days.

(21) Appl. No.: 14/720,550

(22) Filed: May 22, 2015

(65) Prior Publication Data

US 2015/0250679 A1    Sep. 10, 2015

Related U.S. Application Data

(63) Continuation of application No. 14/094,437, filed on Dec. 2, 2013, now Pat. No. 9,072,829, which is a
(Continued)

(51) Int. Cl.
*A61M 37/00* (2006.01)
*A61J 1/20* (2006.01)
(Continued)

(52) U.S. Cl.
CPC .......... *A61J 1/2055* (2015.05); *A61J 1/1406* (2013.01); *A61J 1/2006* (2015.05); *A61M 5/162* (2013.01);
(Continued)

(58) Field of Classification Search
CPC ...... A61M 39/1011; A61M 2039/1027; A61M 2039/1033; A61M 2039/1066;
(Continued)

(56) References Cited

U.S. PATENT DOCUMENTS 4,895,570 A    1/1990 Larkin
5,056,756 A   10/1991 Norkey et al.
(Continued)

FOREIGN PATENT DOCUMENTS

EP    0806597 A1    11/1997
WO   WO-9316315 A1   8/1993
(Continued)

OTHER PUBLICATIONS

Australian Examination Report No. 1 for Application No. 2008260307, dated Feb. 23, 2013, 4 pages.
(Continued)

*Primary Examiner* — Jason Flick
(74) *Attorney, Agent, or Firm* — McDermott Will & Emery LLP (57) ABSTRACT

An attachment arrangement has a housing and a needle located within the housing. The arrangement allows administration ports of different sizes to be inserted into and secured within the housing. In certain embodiments, compliant retainers secure the administration port within the housing. In certain other embodiments, the administration port is secured within the housing when the housing is compressed against the administration port by a housing compression element. Once the administration port is secured within the housing, a fluid-tight seal is formed between the attachment device and the administration port.

16 Claims, 12 Drawing Sheets

Related U.S. Application Data continuation of application No. 11/804,660, filed on May 18, 2007, now Pat. No. 8,597,237.

(51) Int. Cl.
*A61M 5/162* (2006.01)
*A61J 1/14* (2006.01)
*A61M 39/10* (2006.01)
*A61M 39/12* (2006.01)

(52) U.S. Cl.
CPC ......... *A61M 39/1011* (2013.01); *A61M 39/12* (2013.01)

(58) Field of Classification Search
CPC .......... A61M 2039/1077; A61M 39/10; A61M 39/12; A61M 5/158; A61M 5/162; A61M 5/14; Y10S 604/905; Y10S 128/912
USPC .......................................................... 604/86
See application file for complete search history.

(56) References Cited

U.S. PATENT DOCUMENTS

| | | | |
|---|---|---|---|
| 5,201,717 A | 4/1993 | Wyatt et al. | |
| 5,356,396 A | 10/1994 | Wyatt et al. | |
| 5,405,340 A | 4/1995 | Fageol et al. | |
| 5,514,117 A * | 5/1996 | Lynn | A61M 5/158 604/536 |
| 5,924,746 A | 7/1999 | Fixemer | |
| 6,142,446 A | 11/2000 | Leinsing | |
| 7,824,393 B2 * | 11/2010 | Fangrow | A61M 39/26 604/256 |
| 2006/0149211 A1 | 7/2006 | Simpson et al. | |

FOREIGN PATENT DOCUMENTS

| | | |
|---|---|---|
| WO | WO-9423775 A1 | 10/1994 |
| WO | WO-2006036192 A1 | 4/2006 |
| WO | WO-2006052655 A2 | 5/2006 |

OTHER PUBLICATIONS

Canadian Office Action for Application No. 2687663, dated Mar. 31, 2015, 4 pages.
Canadian Office Action for Application No. 2687663, dated May 6, 2014, 2 pages.
Communication Relating to the Results of the Partial International Search.
European Office Action for European Application No. 08755719.5, dated May 13, 2015, 4 pages.
European Office Action for European Application No. 08755719.5, dated Nov. 15, 2011, 5 pages.
International Preliminary Report on Patentability dated Nov. 3, 2009.
International Search Report and Written Opinion for Application No. PCT/US2008/063917, dated Dec. 22, 2008, 13 pages.
Notification of Reasons for Rejection for Japanese Patent Application No. 2010-508607 dated Feb. 5, 2013.

* cited by examiner

UNIVERSAL NEEDLEFREE BAG ACCESS DEVICE

CROSS-REFERENCE TO RELATED APPLICATIONS

The present application is a continuation of U.S. patent application Ser. No. 14/094,437, filed Dec. 2, 2013, entitled, "UNIVERSAL NEEDLEFREE BAG ACCESS DEVICE," which is a continuation of Ser. No. 11/804,660, filed May 18, 2007, now U.S. Pat. No. 8,597,237, entitled, "UNIVERSAL NEEDLEFREE BAG ACCESS DEVICE," the entirety of which is incorporated herein by reference.

BACKGROUND

In the medical field, medical professionals often need to administer various fluids to patients. For example, medications are commonly administered to a patient intravenously in fluid form, as opposed to oral administration. Typically, the intravenous fluid administration takes place at periodic intervals over a length of time. To avoid repeated direct injections into the patient, a catheter is often inserted into the patient's vein. The catheter is then left in place with a receiver portion left protruding out of the patient. Thus, only the receiver portion needs to be accessed in order to administer fluid into the patient. This method of fluid administration eliminates the need to repeatedly inject the patient, which is not only painful for the patient, but increases the risk for complications.

To administer the fluid to the patient via the catheter, a fluid source must be accessed. Generally, the fluid is held in a bag or similar container that must somehow be accessed, and then connected to the patient's catheter, usually via a fluid line.

Various types of attachment devices are available to access the bag holding the fluid. Attachment devices for removing fluid from a bag, or injecting fluid into a bag, are well known in the field. In general, they are relatively easy and efficient to use. Typically, such an attachment device includes a housing with connection ports at both ends. One end connects to the administration port of the bag holding the fluid, and the other end connects to a fluid line that eventually delivers the fluid to the patient. The fluid can then travel from the bag, through the attachment device, and through a fluid line to the patient.

While current attachment devices are an improvement over older methods of accessing bags, they are not without their problems. One of the biggest problems with existing attachment devices is that manufacturers of the devices generally make attachment devices that are only compatible with that manufacturer's bags. Thus, existing attachment devices are proprietary, and are not designed to be universal attachment devices.

This is especially troublesome in the medical field, where nurses and doctors often work in emergency situations. In these time-sensitive situations, medical professionals do not have a great deal of time to find an attachment device appropriately configured to be compatible with a particular administration port.

Therefore, there is a strong need for a universal attachment device that will work with a wide range of bags from various manufacturers. This will increase efficiency in the medical field, benefiting both the medical professionals who use the attachment devices and the patients who require an intravenous fluid administration.

SUMMARY

The above and other needs are met by the disclosed embodiments which provide an attachment arrangement for attaching a connector to an administration port of a fluid container. The attachment arrangement comprises a housing having a receiving chamber, which is configured to receive the administration port. The receiving chamber includes a wall. The attachment arrangement also includes at least one compliant retainer within the housing. The retainer is configured to comply with the administration port when the administration port is inserted into the housing. The compliant retainer also secures the administration within the housing. The attachment arrangement further includes a needle, which is at least partially within the housing. The needle is configured to pierce the administration port upon insertion of the administration port into the housing.

The earlier stated needs and others are met by still other disclosed embodiments which provide an attachment arrangement comprising a housing having a receiving chamber. The receiving chamber is configured to receive the administration port. The housing also includes a compressible outer housing surface, which is configured to be compressed inwardly towards the center of the receiving chamber. The compressible outer housing surface secures the administration port in the receiving chamber. The attachment arrangement also includes a housing compression element mounted on the outer housing surface. The housing compression element is configured to interact with the outer housing surface to compress the housing inwardly toward the center of the receiving chamber. The attachment arrangement further includes a needle at least partially within the housing. The needle is configured to pierce the administration port upon insertion of the administration port into the housing.

The foregoing and other features, aspects and advantages of the disclosed embodiments will become more apparent from the following detailed description and accompanying drawings.

DETAILED DESCRIPTION

It is contemplated that the subject matter described herein may be embodied in many forms. Accordingly, the embodiments described in detail below are the presently preferred embodiments, and are not to be considered as limitations.

The disclosed embodiments address problems related to the proprietary nature of current attachment devices and the concerns these cause in time critical situations. The disclosed embodiments solve these problems, at least in part, by providing an attachment arrangement for attaching a connector to an administration port of a fluid container. The attachment arrangement comprises a housing having a receiving chamber configured to receive the administration port. The receiving chamber includes a wall. The attachment arrangement also includes at least one compliant retainer in the housing. The retainer is configured to comply with the administration port when the administration port is inserted into the housing. The compliant retainer also secures the administration port within the housing. The attachment arrangement is configured to accommodate various sizes of administration ports. The attachment arrangement further includes a needle, which is at least partially within the housing. The needle is configured to pierce the administration port upon insertion of the administration port into the housing.

The earlier stated needs and others are met by still other disclosed embodiments which provide an attachment arrangement comprising a housing having a receiving chamber. The receiving chamber is configured to receive the administration port. The housing also includes a compressible outer housing surface, which is configured to be compressed inwardly towards the center of the receiving chamber. The compressible outer housing surface also secures the administration port in the receiving chamber. The attachment arrangement also includes a housing compression element mounted on the outer housing surface. The housing compression element is configured to interact with the outer housing surface to compress the housing inwardly toward the center of the receiving chamber. The attachment arrangement is configured to accommodate various sizes of administration ports. The attachment arrangement further includes a needle at least partially within the housing. The needle is configured to pierce the administration port upon insertion of the administration port into the housing.

Figure 1:
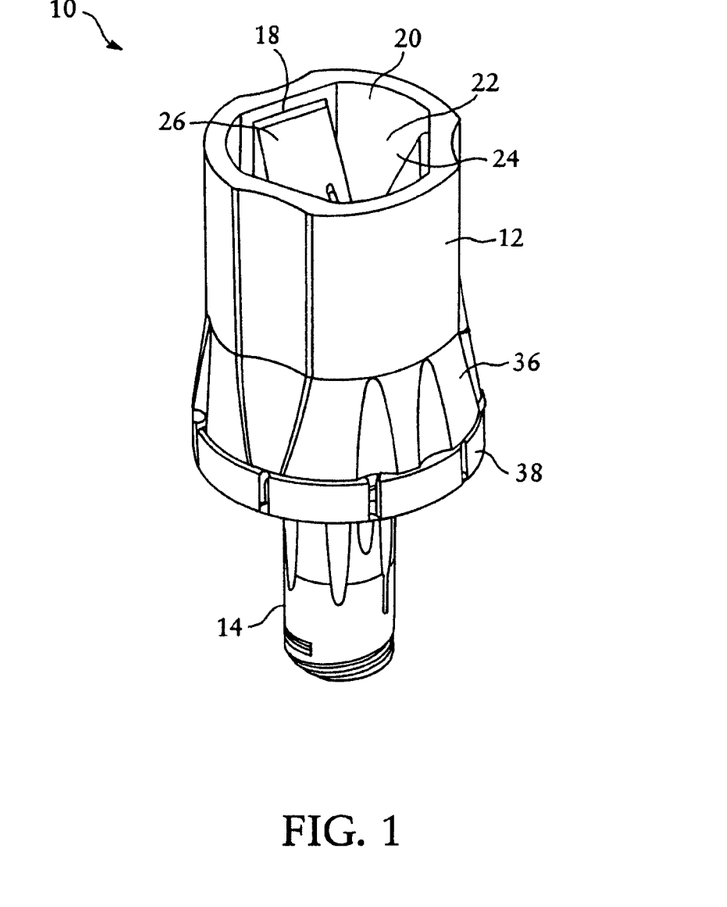
FIG. 1 is a perspective view of one embodiment of the attachment device.
Figure 2:
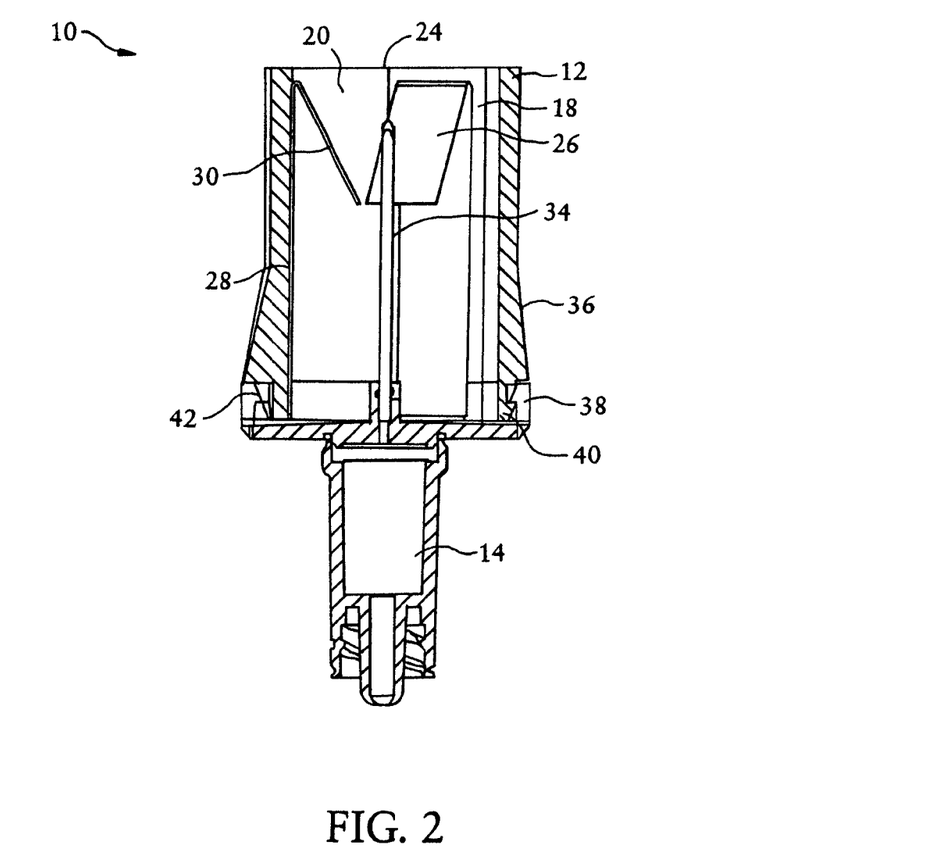
FIG. 2 is a cross-sectional view of the attachment device of FIG. 1.

FIGS. 1 and 2 show an attachment arrangement 10 comprising a housing 12. The attachment arrangement 10 is especially suitable for permanently attaching a connector 14, such as a needlefree connector 14, to an administration port 16 of a fluid container, such as an intravenous (IV) bag (not shown). The housing 12 is generally cylindrically shaped in the illustrated embodiment, though this is exemplary only, as a number of flat wall sections 18 may be provided in addition to curved sections 20. The housing 12 includes a receiving chamber 22 with an insertion opening 24 at one end of the housing 12. An administration port 16 (not shown in FIGS. 1 and 2) is inserted through the insertion opening 24 during use.

Figure 3:
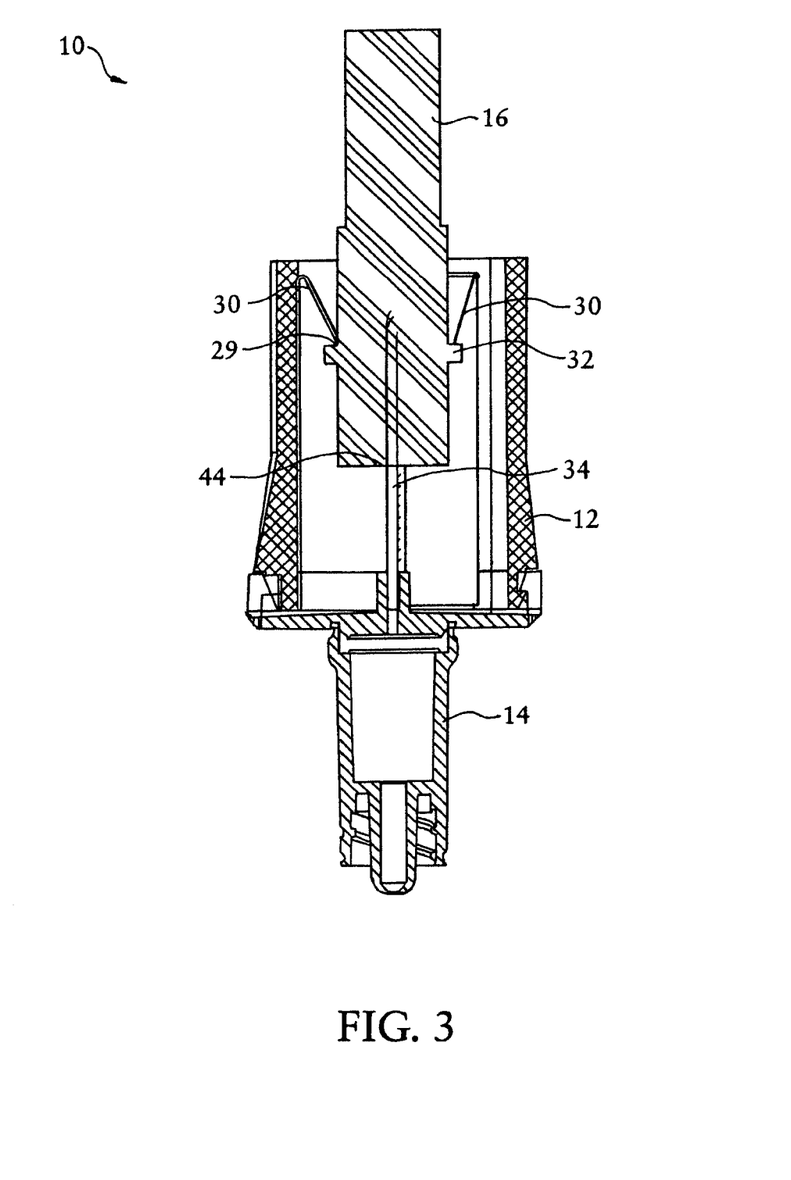
FIG. 3 is a cross-sectional view of the attachment device of FIG. 1 and an administration port.

A plurality of compliant retainers 26 are located within the housing 12. The compliant retainers 26 may be configured as fingers, such as in the exemplary embodiment of FIGS. 1-6, although other configurations may be employed. The compliant retainers 26 are configured and positioned within the housing 12 such that when an administration port 16 is inserted into the housing 12 (as seen in FIG. 3), the compliant retainers 26 will secure the administration port 16 within the housing 12. The housing 12 may be formed from a polymeric material, or any other material. The compliant retainers 26 may be formed from metal; however, any other materials, including a polymeric material, may also be used.

Figure 5:
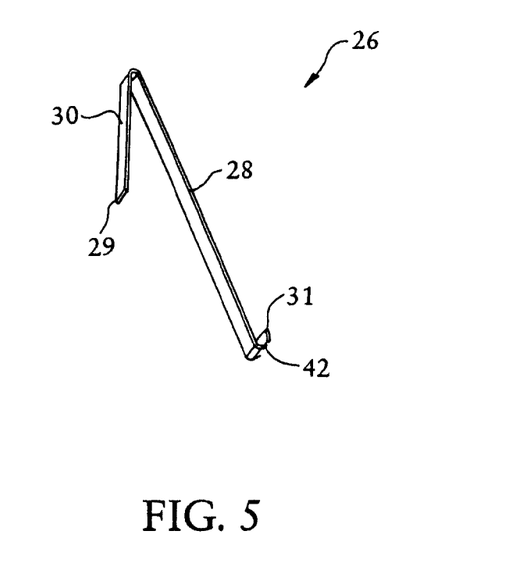
FIG. 5 is a perspective view of the compliant retainer of FIG. 1.

In a preferred embodiment, the compliant retainers 26 may be formed such that they extend along the length of the housing 12 towards the insertion opening 24, then project inwardly from the wall 18 of receiving chamber 22 at a non-perpendicular angle and away from the insertion opening 24. Viewed in FIGS. 1 and 2, the compliant retainers 26 angle downwards and inwards from the top of the housing 12. Referring now also to FIG. 5, the compliant retainers 26 include a first portion 28 that extends along the length of the wall 18, and a second portion 30 that is biased to project inwardly from the receiving chamber wall 18. This second portion 30 is configured to flex towards the receiving chamber wall 18 during insertion of the administration port 16. Hence, administration ports 16 of various sizes, substantially up to the diameter of the insertion opening 24, can be accommodated by the compliant retainers 26. Smaller diameter administration ports 16 will not flex the second portions 30 towards the receiving chamber walls 18 as much as larger diameter administration ports 16. The compliant nature of the second portions 30 allows different sized administration ports 16 to be easily inserted into the housing 12. Hence, the attachment arrangement 10 is able to accommodate administration ports 16 of different manufacturers and makes.

While the compliant retainers 26 are compliant to allow the second portions 30 to flex towards the chamber walls 18, the compliant retainers 26 are generally inflexible in the direction towards the insertion opening 24. Thus, once the administration port 16 has been fully inserted into the housing 12, the compliant retainers 26 will exert a spring-load force on the administration port 16. As shown in FIG. 3, the compliant retainers 26 may flex back to their original position, or as close to their original position as the administration port 16 size will allow, to secure the administration port 16 within the housing 12. Additionally, the compliant retainers 26 may catch a flange 32 (FIG. 3) of the administration port 16 at a second end 29 (FIG. 5) of the compliant retainers 26. Because the compliant retainers 26 are generally inflexible in the upward direction, the administration port 16 may not be easily removed from the housing 12. A plurality of compliant retainers 26 is preferred, as a plurality of compliant retainers 26 will also aid in the alignment of the administration port 16 within the housing 12. However, it is contemplated that a single compliant retainer 26 may secure the administration port 16 within the housing 12.

In another embodiment, once the administration port 16 is fully inserted into the housing 12, the compliant retainers 26 may completely prevent removal of the administration port 16 from the arrangement. Thus, the compliant retainers 26 would permanently secure the administration port 16 within the housing 12.

The attachment device 10 further comprises a needle 34 that is configured to pierce the administration port 16 during insertion of the administration port 16 into the receiving chamber 22. FIG. 2 shows the needle 34 is located within the housing 12. The needle 34 may be formed of metal material, or any other material. As the attachment arrangement 10 provides a needle 34, the attachment device 10 may be used in conjunction with a needlefree connector 14 (FIGS. 1 and 2) that can be secured to the attachment arrangement 10. The needlefree connector 14 may be a closed male luer, such as a Texium™ valve; a needleless female valve, such as a SmartSite® valve; an open male luer; an open female luer; or a drip chamber and IV set directly connected to the attachment arrangement 10.

Figure 4:
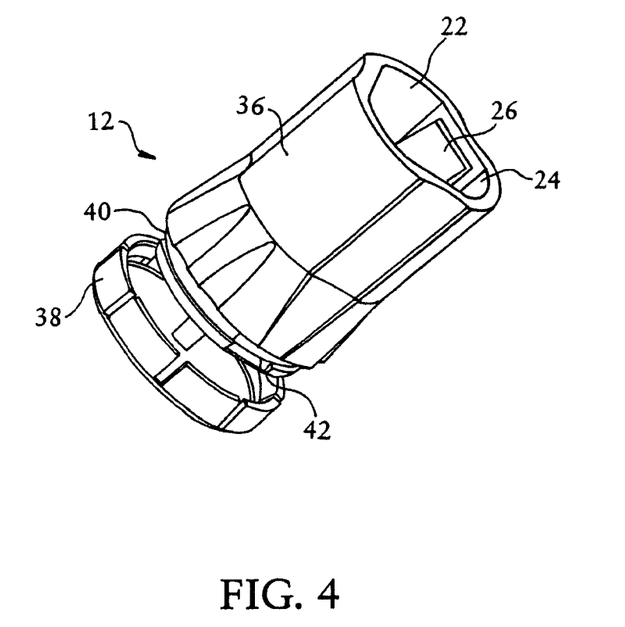
FIG. 4 is a partially-exploded view of the attachment device of FIG. 1.

As shown by FIG. 4, the housing 12 may include two portions, an upper portion 36 and a lower portion 38. The upper portion 36 includes a bottom ridge 40. The lower portion 38 of the housing 12 can then be connected to the bottom ridge 40, thereby connecting the lower portion 38 of the housing 12 to the upper portion 36 of the housing 12. The lower portion 38 may be connected to the bottom ridge 40 of the upper portion 36 by a snap feature, screw threads, adhesive bonding, welding, fasteners, or any other means of attachment. The lower portion 38 of the housing 12 may permanently attach to the upper portion 36 of the housing 12. While manufacturing of the attachment device 10 is made easier by forming the housing 12 from at least two portions, it is contemplated that the housing 12 may include only one portion.

Figure 6:
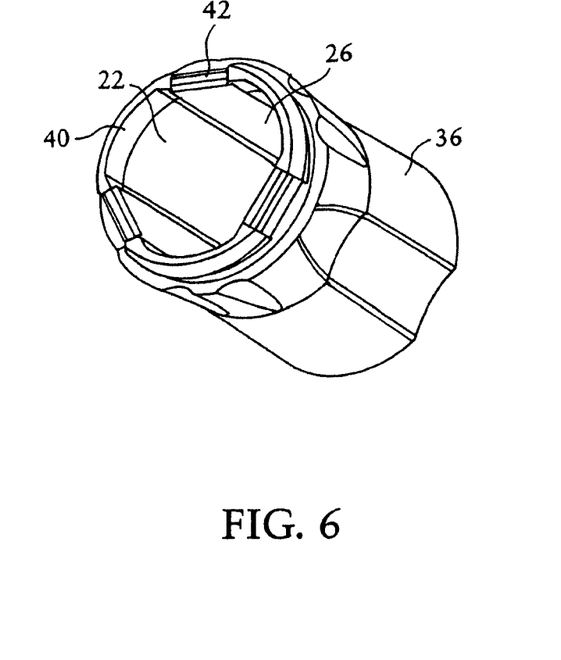
FIG. 6 is a bottom-perspective view of the upper portion of the housing of FIG. 1.

FIG. 5 shows that the compliant retainers 26 may include a connecting portion 42 at a first end 31 of the compliant retainers 26. As shown by FIGS. 4 and 6, the connecting portion 42 may be configured so that it can connect to the bottom ridge 40 of the upper portion 36 of the housing 12. In the embodiment of FIGS. 1-6, the connecting portion 42 is generally hook-shaped. The connecting portion 42 may connect to the bottom ridge 40 by wrapping under and around the bottom ridge 40. When the lower portion 38 of the housing 12 is connected to the bottom ridge 40 of the housing 12, the lower portion 38 will secure the compliant retainers 26 to the housing 12 by enclosing the connecting portion 42 around the bottom ridge 40. If the lower portion 38 is permanently attached to the upper portion 36, the connecting portion 42 of the compliant retainers 26 would also be permanently attached to the bottom ridge 40 of the upper portion 36 of the housing 12.

When the administration port 16 is fully inserted and secured into the housing 12, a fluid-tight seal 44 may be formed between the attachment device 10 and the administration port 16. The fluid-tight seal 44 prevents fluid from escaping as fluid travels through the administration port 16 and the attachment arrangement 10. Thus, patients will receive the correct dosage of fluid. The fluid-tight seal 44 also serves to protect caregivers from unintended exposure to the drugs.

Figure 7:
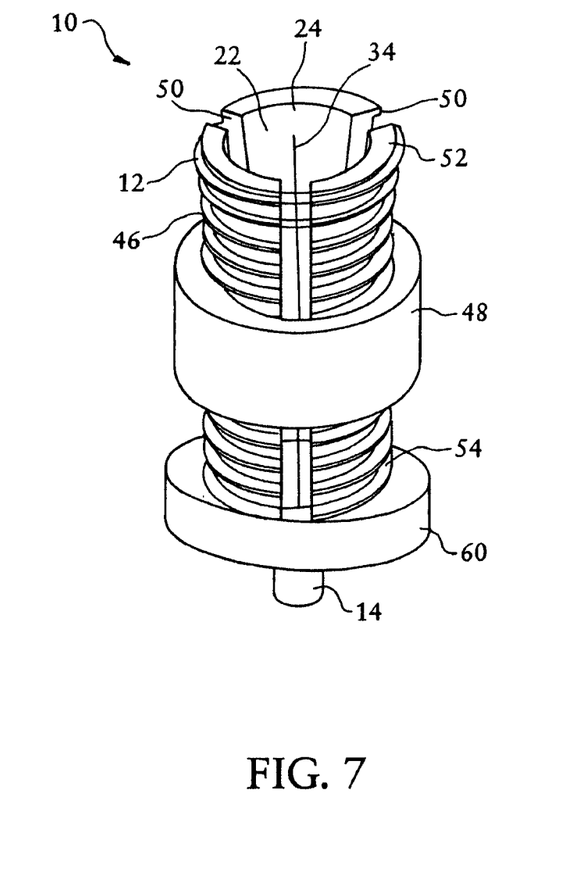
FIG. 7 is a perspective view of another embodiment of the attachment device.

FIG. 7 shows another embodiment of the attachment arrangement 10, in which the housing 12 includes a compressible outer housing surface 46. The compressible outer housing surface 46 is configured to be compressed inwardly, towards the center of the receiving chamber 22. The compression of the outer housing surface 46 allows the housing 12 to essentially enclose around and secure the administration port 16 in the receiving chamber 22. Thus, the housing 12 is flexible, and works to accommodate various sizes of administration ports 16 within the receiving chamber 22.

The attachment arrangement 10 further includes a housing compression element 48 mounted on the outer housing surface 46. The housing compression element 48 is configured to interact with the outer housing surface 46 to compress the housing 12 inwardly toward the center of the receiving chamber 22. Thus, while the outer housing surface 46 is compressible, manipulation of the housing compression element 48 is what causes the outer housing surface 46 to compress and secure the administration port 16.

The housing 12 is substantially cylindrical in shape. However, it is contemplated that the housing 12 may be shaped in a non-cylindrical geometry as well. The housing 12 includes at least one axial slit 50; however, a plurality of axial slits 50 may be included. The axial slit 50 extends along the length of the housing 12, and it provides the housing 12 with flexibility.

Upon insertion of the administration port 16 into the receiving chamber 22, the axial slit 50 allows the housing 12 to flex open in the outward direction. This enables the receiving chamber 22 to receive and accommodate a variety of different sized administration ports 16, including larger sized ones. Of course, if a smaller administration port 16 is used, there may not be a need for the housing 12 to flex in the outward direction.

Additionally, the axial slit 50 also allows the housing 12 to inwardly compress such that the housing 12 may bear on and secure the administration port 16 within the receiving chamber 22. As discussed above, this is beneficial because it allows the housing 12 to secure administration ports 16 of various sizes, and from various manufacturers, within the receiving chamber 22.

The outer housing surface 46 may be threaded with threads, and the housing compression element 48 may be a nut concentrically mounted on the threads. Thus, the nut 48 may be screwed around the outer housing surface 46, compressing and tightening the housing 12 around the administration port 16. The housing 12 may also include a first end 52 with an insertion opening 24 through which the administration port 16 is inserted into the receiving chamber 22. Opposite the first end 52 is a second end 54 of the housing 12. The threads may have a pitch diameter 56 that increases towards the first end 52. The increase in pitch diameter 56 allows for insertion of larger administration ports 16 into the receiving chamber 22. The presence of the axial slit 50 eliminates any looseness created by the larger diameter 56 around an inserted administration port 16, as the axial slit 50 enables the housing 12 to compress around the administration port 16 within the receiving chamber 22, as the nut 48 is moved towards the first end 52. This secures the administration port 16 within the housing 12.

Figure 8:
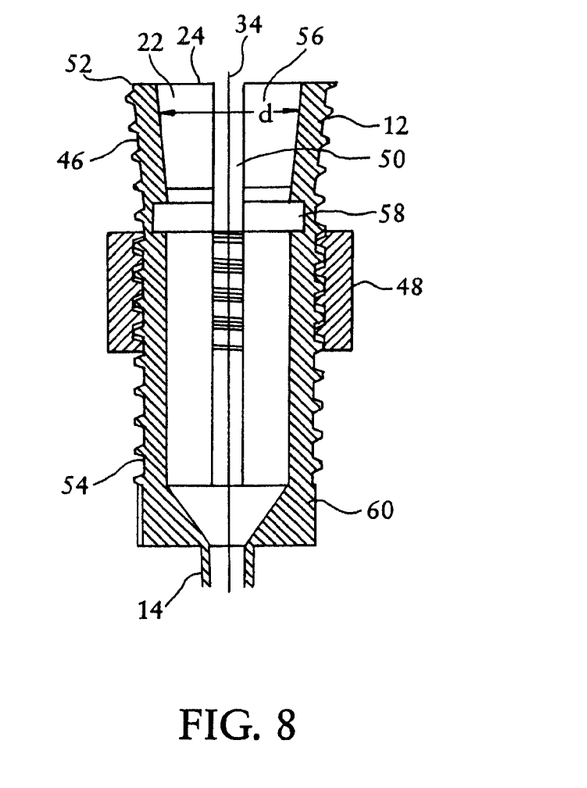
FIG. 8 is a cross-sectional view of the attachment device of FIG. 7.
Figure 9:
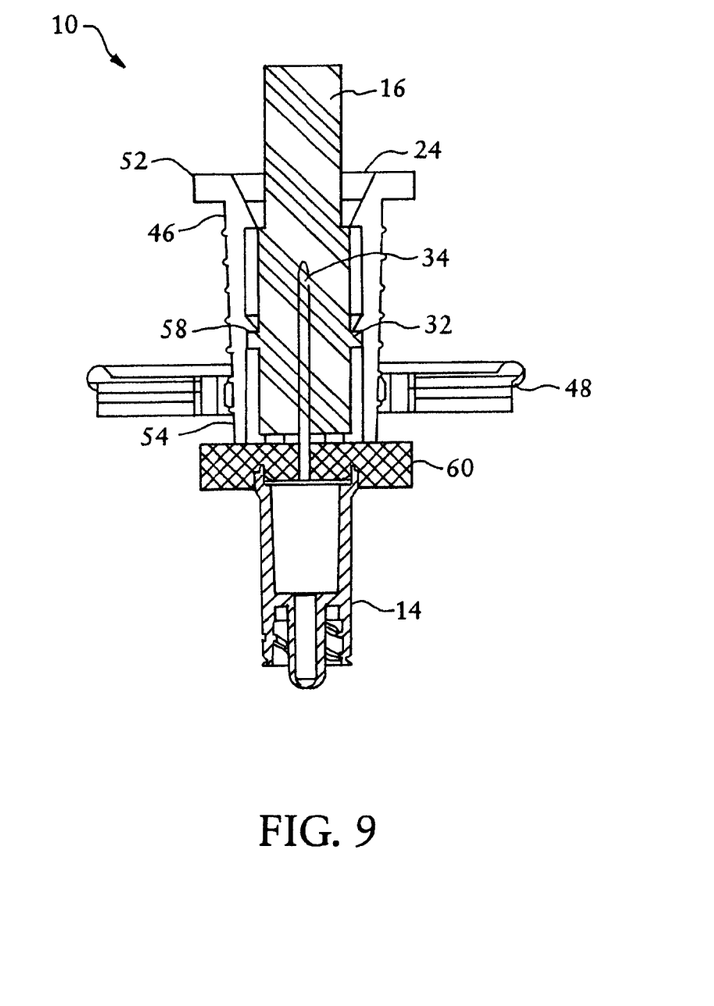
FIG. 9 is a cross-sectional view of the attachment device of FIG. 7 and an administration port.

As shown by FIG. 8, the housing 12 further includes a notch 58, which is located within the receiving chamber 22. The notch 58 is configured to interact with a flange 32 of the administration port 16 (not shown in FIG. 8). As shown by FIG. 9, when the administration port 16 is inserted into the housing 12, the notch 58 grasps the flange 32, further securing the administration port 16 within the housing 12.

The flexibility provided by the axial slit 50 coupled with the larger diameter 56 allows the housing 12 to flex open and outwardly in order to receive an administration port 16. Once the administration port 16 is inserted, and the notch 58 has grasped the flange 32, the housing may flex back to substantially its original position, or as close thereto as the size of the administration port 16 will allow. As shown in FIG. 8, the pitch diameter 56 of the threads increases on the outer housing surface 46 from the notch 58 to the first end 52. Thus, the movement of the nut 48 towards the first end 52 of the housing 12 compresses the housing 12 inwardly. This secures the administration port 16 within the notch 58 of the housing 12.

As shown in FIG. 7, the outer housing surface 46 may also include a flange 60 remote from the first end 52. The flange 60 is configured and located such that a user may grasp onto it during rotation of the nut 48 around the housing 12. This ensures easy and efficient use of the attachment arrangement 10.

Figure 10:
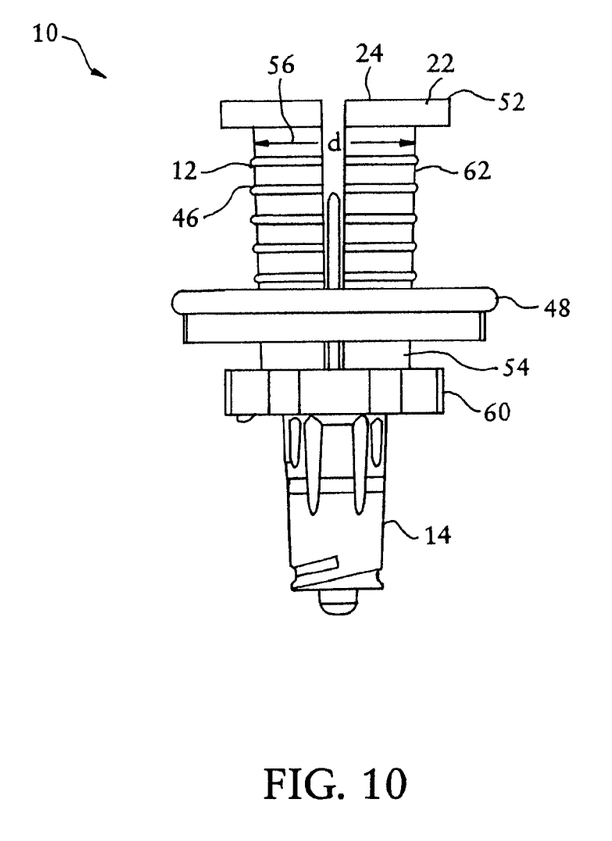
FIG. 10 is a side view of another embodiment of the attachment device.
Figure 11:
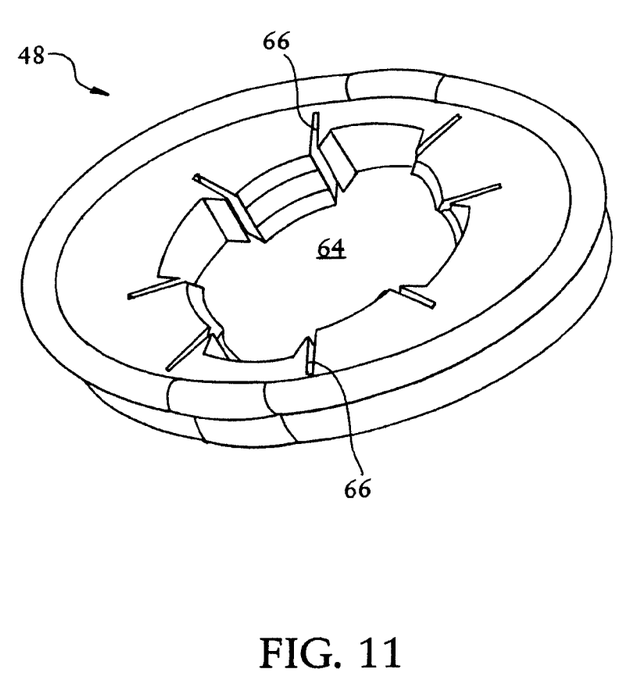
FIG. 11 is perspective view of the slip ring of FIG. 10.

As shown in FIGS. 10-11, in another embodiment, the housing 12 may not be threaded. The housing compression element 48 is a slip ring 48 concentrically mounted on the outer housing surface 46. The outer housing surface 46 includes a plurality of notches 62 between the first and second ends 52, 54. The notches 62 are configured such that movement of the slip ring 48 towards the first end 52 of the housing 12 when the administration port 16 is within the receiving chamber 22 compresses the housing 12 inwardly. Thus, depending on the size of the administration port 16, the slip ring 48 would fit into a different notch 48.

The slip ring 48, shown in FIG. 11, may include an opening 64. The opening is formed such that it may slide over the flange 60. As shown in FIG. 10, the flange may include four separate segments. Thus, the opening 64 may be shaped to include four corresponding cut-outs. The cut-outs may be aligned with the four segments such that the slip ring 48 may be slipped over the housing 12. Once the slip ring 48 surrounds the housing 12, it may be rotated forty-five degrees such that it cannot be removed without an additional rotation. The slip ring 48 further includes radially spaced slits 66 surround the opening. The slits 66 allow the slip ring 48 to have more flexibility when sliding over the housing 12.

Figure 12:
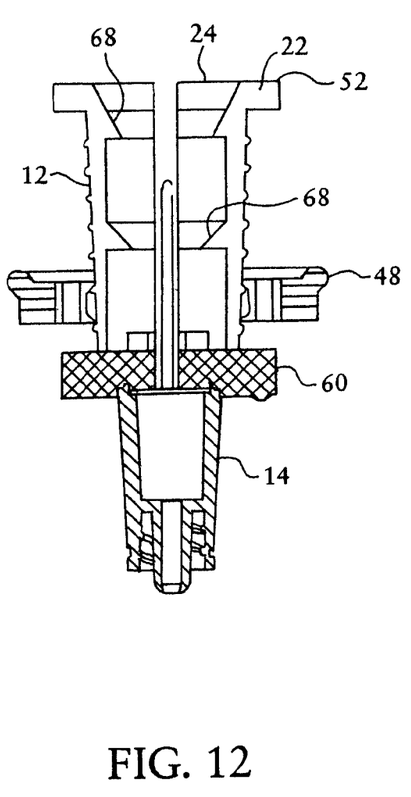
FIG. 12 is cross-sectional view of the attachment device of FIG. 10.

Additionally, as shown in FIG. 12, the housing 12 may be formed such that it may accommodate a variety of lengths of administration ports 16. At least two undercuts 68 may be located inside the housing 12 to accommodate for the variously sized administration ports 16.

What is claimed is:

1. An attachment arrangement for attaching a connector to an administration port of a fluid container, comprising:
    a housing having a receiving chamber configured to receive the administration port at a first end;
    a compressible outer housing surface configured to (i) flex outwardly upon insertion of the administration port into the receiving chamber, and (ii) to be compressed inwardly towards a center of the receiving chamber and to secure the administration port in the receiving chamber;
    a plurality of protrusions on the outer housing surface, the protrusions spaced apart along a longitudinal axis of the housing and having a diameter that increases towards the first end; and
    a housing compression element comprising a ring that engages the protrusions to compress the outer housing surface inwardly as the ring is sequentially advanced toward the first end.

2. The attachment arrangement of claim 1, wherein the housing compression element is a slip ring concentrically mounted on the outer housing surface such that movement of the slip ring towards the first end of the housing compresses the housing inwardly.

3. The attachment arrangement of claim 1, wherein the outer housing surface comprises a discontinuous surface separated by axially extending slits.

4. The attachment arrangement of claim 3, wherein the discontinuous surface comprises a plurality of semi-cylindrical members.

5. The attachment arrangement of claim 1, further comprising a needle at least partially within the housing and configured to pierce the administration port upon insertion of the administration port into the housing.

6. The attachment arrangement of claim 1, further comprising a notch within the receiving chamber, the notch configured to interact with a flange of the administration port.

7. The attachment arrangement of claim 1, wherein the outer housing surface has a flange remote from the first end, the flange configured for grasping by a user during advancement of the housing compression element.

8. The attachment arrangement of claim 1, wherein the housing compression element includes radially spaces slits around an opening.

9. A method of attaching a connector to an administration port of a fluid container, comprising the steps of:
    inserting the administration port into a receiving chamber at a first end of a housing such that a compressible outer housing surface flexes outwardly, wherein the compressible outer housing surface comprises a plurality of protrusions spaced apart along a longitudinal axis of the housing and having a diameter that increases towards the first end;
    grasping a flange of the outer housing surface, wherein the flange is remote from the first end; and
    advancing a housing compression element toward the first end, and away from the flange, such that engagement of the housing compression element with the protrusions compresses the outer housing surface inwardly towards a center of the receiving chamber to secure the administration port in the receiving chamber.

10. The method of claim 9, wherein the housing compression element is a slip ring concentrically mounted on the outer housing surface such that movement of the slip ring towards the first end of the housing compresses the housing inwardly.

11. The method of claim 9, wherein the outer housing surface comprises a discontinuous surface separated by axially extending slits.

12. The method of claim 11, wherein the discontinuous surface comprises a plurality of semi-cylindrical members.

13. The method of claim 9, further comprising the step of piercing the administration port, upon insertion of the administration port into the housing, with a needle at least partially within the housing upon insertion of the administration port into the housing.

14. The method of claim 9, further comprising the step of engaging a flange of the administration port, upon insertion of the administration port into the housing, with a notch within the receiving chamber.

15. The method of claim 9, comprising grasping the flange of the outer housing surface during advancement of the housing compression element.

16. The method of claim 9, wherein the housing compression element includes radially spaces slits around an opening.

* * * * *